US012228563B2

United States Patent
Xu et al.

(10) Patent No.: US 12,228,563 B2
(45) Date of Patent: Feb. 18, 2025

(54) INTEGRATED TEST DEVICE AND METHOD FOR FILLING KARST CAVE DEPOSITION AND TUNNEL INTERMITTENT WATER AND MUD INRUSH DISASTERS

(71) Applicant: SHANDONG UNIVERSITY, Shandong (CN)

(72) Inventors: Zhenhao Xu, Jinan (CN); Xin Huang, Jinan (CN); Youbo Liu, Jinan (CN); Huihui Xie, Jinan (CN); Tengfei Yu, Jinan (CN); Yanhui Ge, Jinan (CN); Peng Lin, Jinan (CN); Dongdong Pan, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 425 days.

(21) Appl. No.: 17/604,094

(22) PCT Filed: Jan. 21, 2020

(86) PCT No.: PCT/CN2020/073570
§ 371 (c)(1),
(2) Date: Oct. 15, 2021

(87) PCT Pub. No.: WO2020/211505
PCT Pub. Date: Oct. 22, 2020

(65) Prior Publication Data
US 2022/0205971 A1    Jun. 30, 2022

(30) Foreign Application Priority Data
Apr. 15, 2019  (CN) .......................... 201910301148.1

(51) Int. Cl.
*G01N 33/24* (2006.01)
*G09B 23/40* (2006.01)

(52) U.S. Cl.
CPC .......... *G01N 33/246* (2013.01); *G09B 23/40* (2013.01)

(58) Field of Classification Search
CPC ....... G01N 33/24; G01N 33/246; G09B 23/40
See application file for complete search history.

(56) References Cited

U.S. PATENT DOCUMENTS

2019/0206279 A1* 7/2019 Li .......................... G01V 99/00
2020/0400644 A1* 12/2020 Li .......................... G09B 23/40

FOREIGN PATENT DOCUMENTS

| CN | 202204661 U |   | 4/2012 |
| CN | 104807960 A | * | 7/2015 |

(Continued)

OTHER PUBLICATIONS

English Translation of CN-104807960-A (Year: 2015).*

(Continued)

*Primary Examiner* — Alexander A Mercado
(74) *Attorney, Agent, or Firm* — Oliff PLC

(57) ABSTRACT

An integrated test device and method for filling karst cave deposition and tunnel intermittent water and mud inrush disasters. The device includes a mixing tank, water tank, water collection tank and plurality of depositing tanks, wherein mixing tank outlet is connected to one end of a pipe, the other end of the pipe extends to one end of the water tank, the plurality of depositing tanks are arranged underwater tank at intervals, the water collection tank is arranged at the water tank's other end, and a detachable baffle is arranged in the water tank and in front of each depositing tank. The deposition and consolidation of filling media and water and mud inrush can be simulated and observed through the setting and cooperation of the plurality of depositing tanks, different working conditions can be simu- (Continued)

lated by changing the flow rate, sample concentration, particle gradation, depositing height and displacement.

6 Claims, 3 Drawing Sheets

(56) References Cited

FOREIGN PATENT DOCUMENTS

| | | |
|---|---|---|
| CN | 105004509 A | 10/2015 |
| CN | 106023761 A | 10/2016 |
| CN | 205643028 U | 10/2016 |
| CN | 106197944 A | 12/2016 |
| CN | 206420738 U | 8/2017 |
| CN | 107144470 A | 9/2017 |
| CN | 207036388 U | 2/2018 |
| CN | 108020489 A | 5/2018 |
| CN | 108196006 A | 6/2018 |
| CN | 110047368 A | 7/2019 |
| JP | 2012-018015 A | 1/2012 |

OTHER PUBLICATIONS

Apr. 17, 2020 International Search Report issued in International Patent Application No. PCT/CN2020/073570.

Apr. 17, 2020 Written Opinion issued in International Patent Application No. PCT/CN2020/073570.

Feb. 28, 2020 Search Report isssued in Chinese Patent Application No. 201910301148.1.

Yi Zhou et al. "3D Fluid-Solid Coupled Model Test on Water-Inrush in Tunnel Due to Seepage From Filled Karst Conduit". Chinese Journal of Rock Mechanics and Engineering, vol. 34, No. 9, 2015, pp. 1739-1749.

Qing-song Zhang et al. "Development and Application of Model Test System for Inrush of Water and Mud of Tunnel in Fault Rupture Zone". Chinese Journal of Geotechnical Engineering, vol. 39, No. 3, 2017, pp. 417-426.

De-ming Wang et al. "Model Experiment on Inrush of Water and Mud and Catastrophic Evolution in a Fault Fracture Zone Tunnel". Rock and Soil Mechanics, vol. 37, No. 10, 2016, pp. 2851-2860.

\* cited by examiner

INTEGRATED TEST DEVICE AND METHOD FOR FILLING KARST CAVE DEPOSITION AND TUNNEL INTERMITTENT WATER AND MUD INRUSH DISASTERS

FIELD OF THE INVENTION

The present disclosure relates to an integrated test device and method for filling karst cave deposition and tunnel intermittent water and mud inrush disasters.

BACKGROUND OF THE INVENTION

The statement of this section merely provides background art information related to the present disclosure, and does not necessarily constitute the prior art. It is understood that karst disaster-causing systems account for 45% of tunnel water and mud inrush disasters. It is difficult to find out all bad geological conditions of deep and long tunnels (caves) in karst regions along the line in the early stage of construction, the cause of sudden disasters and the catastrophic process are extremely complicated, and the tunnel construction in karst regions often encounters water and mud inrush and ground collapse, which affect the construction progress and cause safety accidents.

The structural mechanism of the karst tunnel water and mud inrush disaster-causing systems are relatively complicated, the disaster-pregnant mechanism, cause mechanism, disaster mode and evolution process of disasters in karst tunnels are obviously different from those of disasters in other regions and other geotechnical engineering, and the prevention theories and technical methods cannot apply existing theories and techniques. Therefore, during the construction of tunnels (caves), it is very important to study the formation mechanism and evolution process of karst caves in front of tunnel faces in karst regions.

At present, many domestic and foreign scholars have carried out effective research on engineering properties of rock and soil in karst regions and disaster-pregnant mechanisms and evolution processes of tunnel water and mud inrush disasters in terms of dealing with water and mud inrush problems in karst tunnels, but the research mostly focuses on actual engineering monitoring and numerical simulation. The actual engineering monitoring is undoubtedly the most objective and direct research method. However, the disaster-pregnant law of internal karst caves cannot be seen during the actual monitoring, and the actual monitoring is easily interfered by multiple solutions of an actual detection target, so it is difficult to obtain ideal test results. The numerical simulation method is a method of abstracting a numerical model from an actual research object for research, so its experimental results have large errors.

At the same time, according to the inventors' understanding, in many tunnel water and mud inrush model tests at present, media are still artificially filled in karst caves based on particle gradation, which is quite different from the actual formation process of karst cave filling media. In addition, there is no test device that simulates the deposition process of a karst cave under natural conditions, and tunnel water and mud inrush occurring after the deposition of karst cave filling media under natural conditions cannot be simulated.

SUMMARY OF THE INVENTION

In order to solve the above problems, the present disclosure proposes an integrated test device and method for filling karst cave deposition and tunnel intermittent water and mud inrush disasters. The present disclosure can simulate the deposition of filling media in large karst caves and reproduce the occurrence of intermittent water and mud inrush disasters in tunnels, which is conducive to studying the influencing factors of intermittent water and mud inrush in tunnels.

According to some embodiments, the present disclosure adopts the following technical solutions: An integrated test device for filling karst cave deposition and tunnel intermittent water and mud inrush disasters, including a mixing tank, a water tank, a water collection tank and a plurality of depositing tanks, wherein an outlet of the mixing tank is connected to one end of a pipe, the other end of the pipe extends to one end of the water tank, the plurality of depositing tanks are arranged under the water tank at intervals, the water collection tank is arranged at the other end of the water tank, and a detachable baffle with a different caliber is arranged in the water tank and in front of each depositing tank;

A valve, a flowmeter and a recorder are arranged on the pipe, the valve is used to control the flow rate and flow volume of a mud-water mixture after mixing, and the flowmeter and the recorder are used to calculate an outflow and a flow rate profile of the mud-water mixture in the mixing tank per unit time;

The depositing tank is connected with the water tank by a flange structure, a permeable plate and a permeable stone are arranged at a bottom of the depositing tank, a switch is arranged on one side of the depositing tank, an articulated joint is arranged on the other side of the depositing tank, the articulated joint is connected to the pipe, a control valve is arranged between the articulated joint and the depositing tank, and a camera is arranged on the pipe to capture water and mud inrush in the depositing tank for analyzing and calculating the displacement-strain law of particles in a depositing sequence and the widths of cracks in the depositing sequence.

The present disclosure can simulate and observe the deposition and consolidation of filling media and the water and mud inrush through the plurality of depositing tanks, simulate different working conditions by changing the flow rate, sample concentration, particle gradation, depositing height and displacement (put into the corresponding depositing tank), and well study the intermittent water and mud inrush.

As one or more embodiments, the pipe at the outlet of the mixing tank flushes with the water tank. The same height of the pipe and the water tank can ensure smooth flowing of the mixture and eliminate interference factors.

As one or more embodiments, a water tank baffle with a certain height is arranged at a tail end of the water tank to ensure that water flow in the water tank has a certain height.

As one or more embodiments, support frames are arranged at two ends of the water tank.

As one or more embodiments, an outlet is arranged at a bottom of the water collection tank, and the outlet is connected to a drain pipe that can lead to a sewer.

As one or more embodiments, the depositing tank is provided with horizontal scales and vertical scales.

As one or more embodiments, the articulated joint is used to connect the depositing tank and the pipe, and a sealing mechanism is arranged at the joint of the connection to ensure good sealing at the joint.

As one or more embodiments, the permeable stone is arranged on the permeable plate, at least one layer of filter paper covers the permeable stone, water infiltrates the permeable stone during the deposition and consolidation of a filling medium in the depositing tank, and the permeable plate includes a plurality of water flowing channels in an array thereon and a support for supporting the plate to discharge excess water infiltrated during the deposition and consolidation of silt in the depositing tank.

As one or more embodiments, the camera adopts an XTDIC three-dimensional full-field dynamic strain and deformation measurement system as an optical system.

A working method based on the above device includes the following steps:

checking whether each part is working normally, and putting the permeable plate, the permeable stone and the filter paper into each depositing tank in order;

filling the mixing tank with clean water, opening the valve at the water inlet of the water tank, until each depositing tank is filled with water and the water level in the water tank reaches a set height, then preparing a filling medium sample according to the set particle gradation, pouring the sample into the mixing tank and adding a certain amount of water for thorough mixing;

placing the baffles at the inlets of all the depositing tanks except the first depositing tank, and opening a drainage port of the water collection tank;

recording relevant data of the test process with the flowmeter and the recorder, opening the water inlet of the water tank to allow the silt mixture to flow into the water tank while adding the test sample and water into the mixing tank according to a proportion, and closing the valve at the water inlet of the water tank after the silt deposits to a certain height in the first depositing tank;

placing the baffle at the water inlet of the second depositing tank to the water inlet of the first depositing tank, continuing to open the valve at the water outlet such that the silt deposits to the second depositing tank, and carrying out the deposition in the depositing tanks in order according to the same test steps after the silt deposits to a certain height in the second depositing tank;

after the set number of depositing tanks are filled, stopping flushing, standing the sediment, opening the switches at the bottoms of the depositing tanks, and depositing and consolidating the sediment for a period of time; and according to the captured images, analyzing a depositing sequence in the depositing tanks and a displacement-strain law of silt particles during the water and mud inrush.

As a further limitation, after the filling medium in the depositing tank is deposited and consolidated, the pipe is connected, the connection valve between the depositing tank and the pipe is opened, the water and mud inrush is observed, and if the water and mud inrush does not occur, water is added to the depositing tanks and water inrush is recorded.

As a further limitation, after the first water and mud inrush disaster occurs, the distribution of protrusions and the change characteristics of the filling medium in the depositing tanks are observed; water is slowly added to the top of the water and mud inrush, and the water collection process, the time of second water and mud inrush, the status of water inrush are observed.

The influence of flow rate, concentration of the filling medium, displacement or/and particle gradation under different test conditions on the deposition characteristics of the karst cave filling medium and the influence law of particle gradation, water head height or/and deposition height on intermittent water and mud inrush are observed.

Compared with the prior art, the beneficial effects of the present disclosure are:

The present disclosure develops a visual water and mud inrush test device based on the law of karst cave development by using photogrammetry technology, carries out experimental research on karst tunnel filling karst cave depositing sequences and intermittent water and mud inrush disasters, reproduces the deposition of filling media in large karst caves and the process of intermittent water and mud inrush disasters, researches the formation conditions and influencing factors of intermittent water and mud inrush in tunnels, and reveals the occurrence and development law and disaster-causing mechanism of water and mud inrush disasters, and the relevant research results can provide guidance for the prevention and treatment of water and mud inrush disasters when tunnels pass through filling karst caves.

BRIEF DESCRIPTION OF THE DRAWINGS

The accompanying drawings constituting a part of the present disclosure are intended to provide a further understanding of the present disclosure, and the illustrative embodiments of the present disclosure and the descriptions thereof are intended to interpret the present disclosure and do not constitute improper limitations to the present disclosure.

Figure 1:
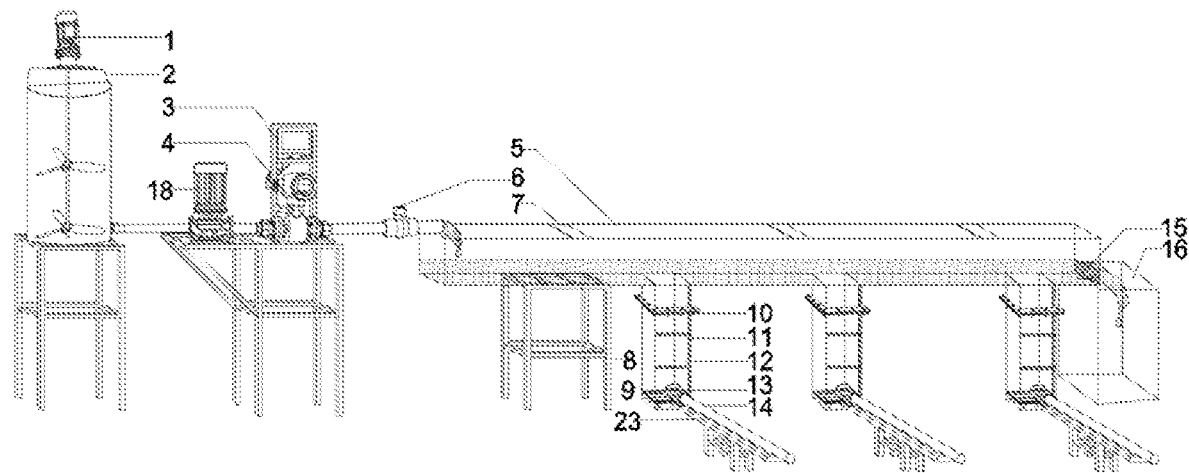
FIG. 1 is an overall schematic diagram of a test device.

In the figures: 1—mixer; 2—mixing tank; 3—paperless recorder; 4—electromagnetic flowmeter; 5—water tank; 6—valve; 7, 15, 20, 21—organic glass plate; 8, 23—support frame 9—permeable plate; 10—flange structure; 11—sticking ruler; 12—depositing tank; 13—articulated joint; 14—round pipe; 16—water collection tank; 17—DIC high-speed camera; 18—water pump; 19—faucet; 22—shovel.

DETAILED DESCRIPTION OF EMBODIMENTS

The present disclosure will be further illustrated below in conjunction with the accompanying drawings and embodiments.

It should be noted that the following detailed descriptions are exemplary and are intended to provide further descriptions of the present disclosure. All technical and scientific terms used herein have the same meanings as commonly understood by those ordinary skilled in the art to which the present disclosure belongs, unless specified otherwise.

It should be noted that terms used herein are intended to describe specific embodiments only rather than to limit the exemplary embodiments according to the present disclosure. As used herein, the singular form is also intended to comprise the plural form unless otherwise indicated in the context. In addition, it should be understood that when the terms "contain" and/or "comprise" are used in the description, they are intended to indicate the presence of features, steps, operations, devices, components and/or combinations thereof.

In the present disclosure, the terms such as "upper", "lower", "left", "right", "front", "rear", "vertical", "horizontal", "side", and "bottom" indicate the orientation or positional relationships based on the orientation or positional relationships shown in the drawings, are only relationship terms determined for the convenience of describing the structural relationships of various components or elements of the present disclosure, but do not specify any component or element in the present disclosure, and cannot be understood as limitations to the present disclosure.

In the present disclosure, the terms such as "fixed", "connected" and "coupled" should be generally understood, for example, the "connected" may be fixedly connected, detachably connected, integrally connected, directly connected, or indirectly connected by a medium. For a related scientific research or technical person in this art, the specific meanings of the above terms in the present disclosure may be determined according to specific circumstances, and cannot be understood as limitations to the present disclosure.

Figure 2:
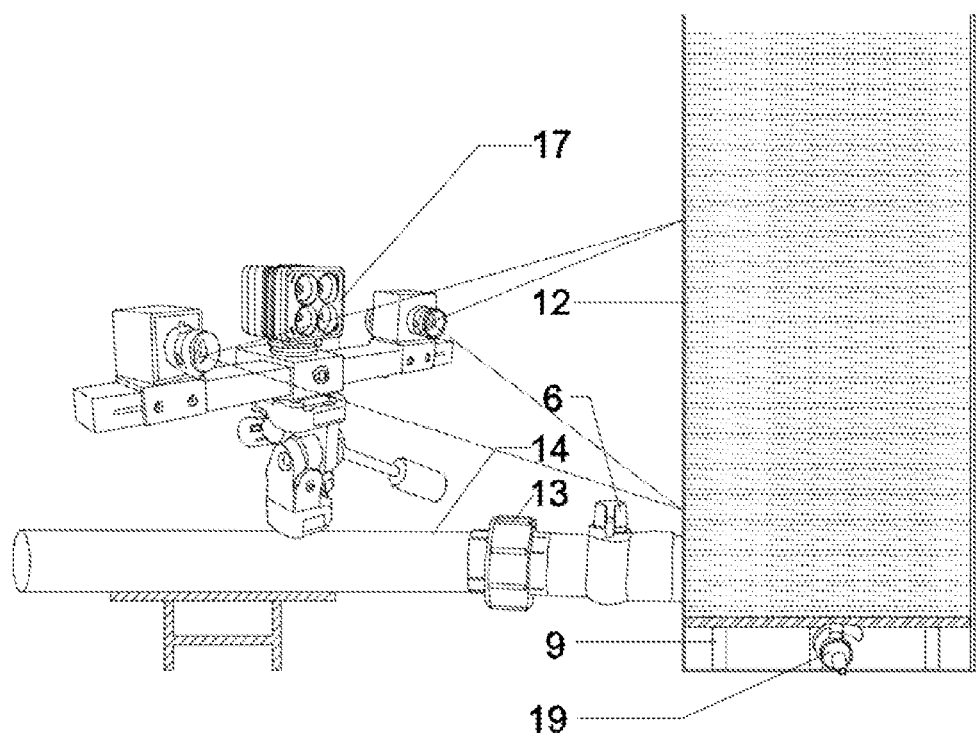
FIG. 2 is a schematic diagram of layout of a DIC high-speed camera and a depositing tank.
Figure 3:
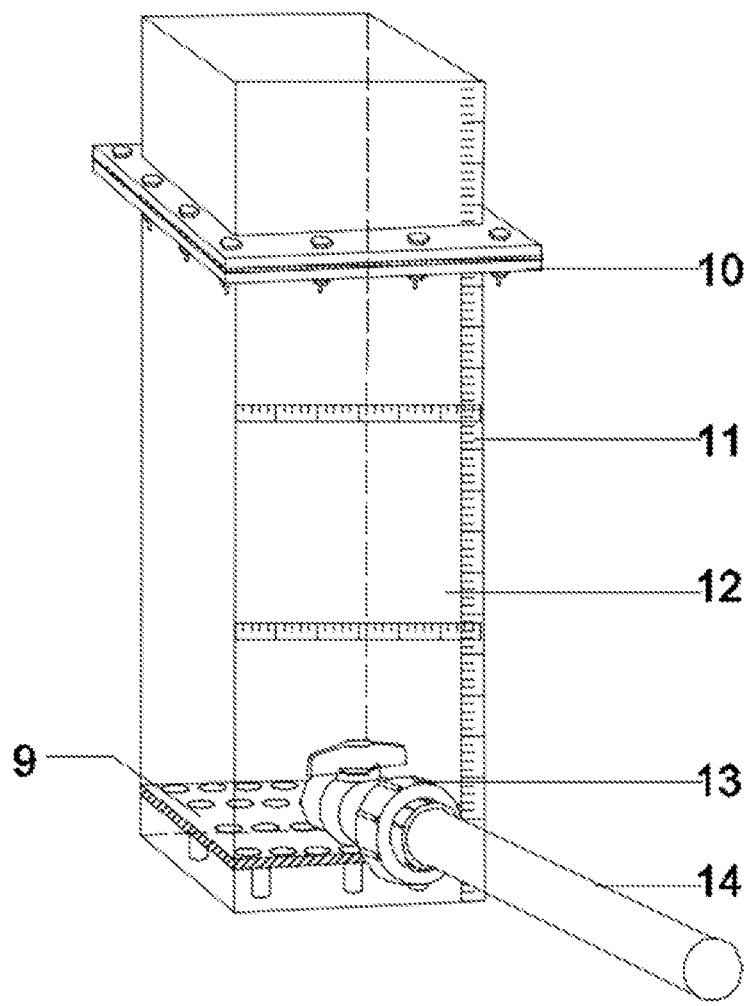
FIG. 3 is a schematic structural diagram of the depositing tank.
Figures 4A, 4B:
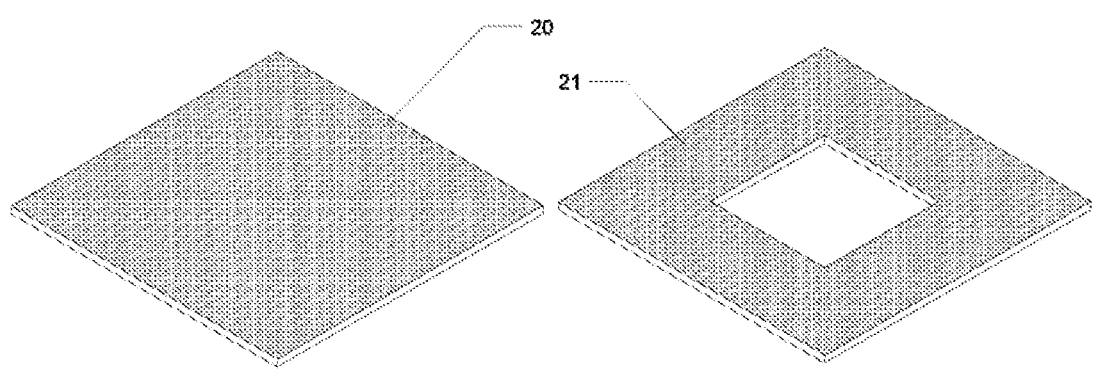
FIG. 4(a) and FIG. 4(b) are schematic structural diagrams of an organic glass baffle.
Figure 5:
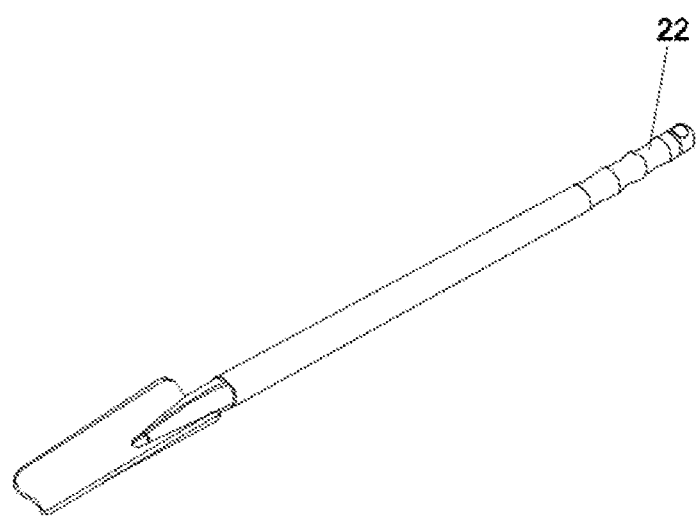
FIG. 5 is a schematic structural diagram of a shovel.

Referring to FIGS. 1 to 5, an integrated test device for filling karst cave deposition and tunnel intermittent water and mud inrush disasters includes a mixing tank 2, a water pump 18, an electromagnetic flowmeter 4, a paperless recorder 3, a water tank 5, a round pipe 14, a tank 12 (depositing tank), a DIC high-speed camera 17, a permeable plate 9, a valve 6, a water collection tank 16 and a support frame 8. The mixing tank 2 is placed on a left side of a water inlet of the water tank 5, wherein the water pump 18, the electromagnetic flowmeter 4 and the paperless recorder 3 are connected to a water outlet of the mixing tank 2, a pipe at the water outlet of the mixing tank 2 flushed with the water tank 5, the water tank 5 and the depositing tank 12 are of a flange connection structure, the valve 6 and an articulated joint 13 are arranged at a bottom of the depositing tank 12 to connect the depositing tank 12 with the round pipe 14, the permeable plate 9 and a permeable stone are placed at an internal bottom of the depositing tank, and the water collection tank 16 is placed on a right side of a water outlet of the water tank 5.

Further, the bottom of the mixing tank 2 is connected with a PPR water outlet pipe, the water pump 18, the electromagnetic flowmeter 4 and the paperless recorder 3 are connected to the water outlet, a valve 6 is arranged at a water inlet of the water tank 5, the flow rate and flow volume of a test sample can be controlled through the valve 6, the mixing tank 2 has a volume of 1000 L, and the electromagnetic flowmeter 4 and the paperless recorder 3 are used to calculate an outflow and a flow rate profile of a mud-water mixture in the mixing tank per unit time.

Further, an organic glass baffle 15 with a height of 10 cm is arranged at a tail end of the water tank to ensure that water flow in the water tank 5 has a certain height, organic glass plates 7 are arranged at a certain distance along a top surface of the water tank to increase the overall rigidity of the water tank, the water tank is made of transparent organic glass, and the organic glass plates have a thickness of 12 mm and a volume of 720 cm*30 cm*30 cm.

Further, the water tank 5 and the depositing tank 12 are of a flange connection structure, one flange connection structure is arranged along the bottom of the water tank 5 every 200 cm, there are three flange connection structures in total, the depositing tank 12 is made of transparent organic glass, the depositing tank has length×width×height of 30 cm*30 cm*100 cm, and each side of the depositing tank is marked with horizontal scales and vertical scales.

Further, the valve 6, the articulated joint 13 and a drainage faucet 19 are arranged at the bottom of the depositing tank, the permeable plate 9 and the permeable stone are placed at the internal bottom of the depositing tank, and an inlet at the top of the depositing tank is designed with a 30 cm*30 cm square organic glass plate 20 and a 30 cm*30 cm perforated organic glass plate 21 with length×width of 15 cm*15 cm. The articulated joint 13 is used to connect the depositing tank 16 and the round pipe 14, a water stop strip is pasted or a rubber pad is placed to the joint to ensure good sealing at the joint, and the round pipe is placed on a stainless steel support frame 23.

Further, the permeable plate 9 with an area of 30 cm*30 cm is arranged at the internal bottom of the depositing tank, there are six supports with a height of 5 cm at the bottom of the permeable plate, the permeable stone is placed on the permeable plate, a layer of filter paper covers the permeable stone, water infiltrates the permeable stone during the deposition and consolidation of a filling medium in the depositing tank 12, and the permeable plate 9 is composed of lattice supports and water flowing channels and facilitates collection and drainage of the infiltrated water for draining excess water infiltrated during the deposition and consolidation of sand in the depositing tank.

Further, the round pipe has a length L of 2 m and a diameter D of 50 mm, the round pipe 14 is made of transparent organic glass, and a retractable shovel 22 slightly smaller than the diameter of the round pipe is made for dredging in the round pipe after first water and mud inrush.

Further, the water collection tank 16 is placed on the right side of the water outlet of the water tank 5, the water collection tank 16 has a volume of 300 L, the outlet at the bottom of the water collection tank is connected with a soft drainage pipe, and the pipe leads to a sewer to avoid pollution of a test site.

Further, the DIC high-speed camera 17 is placed on a side of the depositing tank for capturing to analyze the displacement-strain law of particles in a depositing sequence and calculate the widths of cracks in the depositing sequence, and the DIC high-speed camera 17 adopts an XTDIC three-dimensional full-field dynamic strain and deformation measurement system as an optical system.

An integrated test method for filling karst cave deposition and tunnel intermittent water and mud inrush disasters is characterized by including the following steps:

Step 1, the test device is assembled and cleaned, whether each instrument is working normally is checked, and the permeable plate 9, the permeable stone and the filter paper are put into three depositing tanks 12 in order respectively.

Step 2, the mixing tank 2 is filled with clean water, and the valve 6 at the water inlet of the water tank 5 is opened, until each depositing tank 12 is filled with water and the water level in the water tank 5 flushes with the baffle 15. Then, a filling medium sample is prepared according to the designed particle gradation, the sample is poured into the mixing tank and a certain amount of water is added for thorough mixing.

Step 3, the 30*30 cm square baffle 20 is placed at the inlets of the second and third depositing tanks respectively, and a valve at a drainage port of the water collection tank 16 is opened.

Step 4, a power switch is turned on to supply power to the water pump 18, the electromagnetic flowmeter 4 and the paperless recorder 3, relevant data during test is recorded, the valve at the water inlet of the water tank is opened, a silt mixture flows into the water tank while the test sample and water are added into the mixing tank according to a proportion, and the valve at the water inlet of the water tank is closed after the silt deposits to a certain height in the first depositing tank.

Step 5, the baffle at the water inlet of the second depositing tank is placed to the water inlet of the first depositing tank, the valve at the water outlet continues to be opened such that the silt deposits to the second depositing tank, and the deposition is carried out in the third depositing tank according to the same test steps after the silt deposits to a certain height in the second depositing tank.

Step 6, after all the three depositing tanks are filled, flushing is stopped, the sediment is stood, the switches at the bottoms of the depositing tanks are opened, and the sediment is deposited and consolidated for a period of time.

Step 7, the DIC high-speed camera is placed on one side of the depositing tank to capture a depositing sequence in the depositing tank and a displacement-strain law of silt particles during the water and mud inrush.

After the filling medium in the depositing tank is deposited and consolidated, the round pipe is connected, the valve connecting the depositing tank with the round pipe is opened, and the water and mud inrush is observed. If there is no water and mud inrush, water is added to the depositing tanks and water inrush is recorded.

After the first water and mud inrush disaster occurs, the distribution of protrusions in the receiving devices and the change characteristics of the filling medium in the depositing tanks are observed. Water is slowly added to the top of the water and mud inrush, and the water collection process, the time of second water and mud inrush, the status of water inrush are observed.

The above test steps are repeated to obtain the influence of flow rate, concentration of the filling medium, displacement, particle gradation, etc. under different test conditions on the deposition characteristics of the karst cave filling medium and the influence law of particle gradation, water head height, deposition height, etc. on intermittent water and mud inrush.

Of course, the size parameters of the above-mentioned components can be changed in other embodiments.

The above-mentioned device can simulate different test conditions, and can simulate the deposition of filling media in karst caves and simulate the occurrence of intermittent water and mud inrush disasters according to different variables. This test device can be used for further studying the influence of different particle gradation, inlet area of the depositing tanks, flow rate of the sample, deposition and consolidation time, water head height, etc. on the deposition of the filling media in the karst caves and the process of intermittent water and mud inrush disasters. The device reproduces the deposition of filling media in large karst caves and the process of intermittent water and mud inrush disasters, researches the formation conditions and influencing factors of intermittent water and mud inrush in tunnels, and reveals the occurrence and development law and disaster-causing mechanism of water and mud inrush disasters, and the relevant study results can provide guidance for the prevention and treatment of water and mud inrush disasters when tunnels pass through filling karst caves.

Described above are merely preferred embodiments of the present disclosure, and the present disclosure is not limited thereto. Various modifications and variations may be made to the present disclosure for those skilled in the art. Any modifications, equivalent substitutions, improvements and the like made within the spirit and principle of the present disclosure shall fall within the scope of the present disclosure.

Although the specific embodiments of the present disclosure are described above in combination with the accompanying drawing, the protection scope of the present disclosure is not limited thereto. It should be understood by those skilled in the art that various modifications or variations could be made by those skilled in the art based on the technical solution of the present disclosure without any creative effort, and these modifications or variations shall fall into the protection scope of the present disclosure.

The invention claimed is:

1. A test device for simulating deposition of filling media in karst caves and occurrence of tunnel intermittent water and mud inrush disasters, comprising
a mixing tank,
a water tank,
a water collection tank and a plurality of depositing tanks, wherein an outlet of the mixing tank is connected to one end of a pipe, another end of the pipe extends to one end of the water tank, the plurality of depositing tanks are arranged under the water tank at intervals, the water collection tank is arranged at another end of the water tank, and a position within the water tank at an inlet of each of the plurality of depositing tanks is configured to receive detachable baffles, wherein the detachable baffles have different heights and/or square holes of different size in the middle, and
a valve, a flowmeter and a recorder arranged on the pipe, wherein
the valve is configured to control flow rate and flow volume of a mud-water mixture being poured in and flowing out of the mixing tank, the flowmeter is configured to measure an outflow per unit time of the mud-water mixture flowing out the mixing tank, and the recorder is configured to record a profile of the flow rate of the mud-water mixture flowing out of the mixing tank per unit time, and
each of the plurality of depositing tanks respectively is connected with the water tank by a flange structure, and a permeable plate and permeable stones are arranged at a bottom of each of the depositing tanks respectively, a switch is arranged on one side of each of the plurality of depositing tanks respectively, an articulated joint connected with a tube is arranged on another side of each of the plurality of depositing tanks respectively, a control valve is arranged between the articulated joint and a corresponding one of the plurality of depositing tanks, and a camera is arranged on the tube and configured to capture images of a process of an occurrence of a simulated water and mud inrush disaster in the corresponding one of the plurality of depositing tanks respectively.

2. The test device according to claim 1, wherein a height of the pipe connected to the outlet of the mixing tank is the same as a height of the water tank; or,
a water tank baffle with a predetermined height is arranged at a tail end of the water tank to ensure that water flow in the water tank has the predetermined height; or,
a support frame is respectively arranged below the one end and the other end of the water tank.

3. The test device according to claim 1, wherein outlet drainage port is arranged at a bottom of the water collection tank, and the outlet is connected to a drain pipe.

4. The test device according to claim 1, wherein each of the plurality of depositing tanks respectively is provided with horizontal scales and vertical scales.

5. The test device according to claim 1, wherein the articulated joint is used to connect the corresponding one of the plurality of depositing tanks and a corresponding one of the tube, and a sealing mechanism is arranged at connections to ensure sealing at the connections.

6. The test device according to claim 1, wherein the permeable stone is arranged on the permeable plate, at least one layer of filter paper covers the permeable stone, and water infiltrates through the permeable stone in a process of deposition of a filling medium in each of the plurality of depositing tanks respectively, wherein the permeable plate comprises a plurality of water flowing channels in an array thereon and a support for supporting the permeable plate, and is configured to discharge excess water infiltrated during the deposition and consolidation process of the filling medium in the depositing tank.

* * * * *